United States Patent [19]

Thornfeldt

[11] Patent Number: 6,071,543
[45] Date of Patent: Jun. 6, 2000

[54] PYRIDINE-THIOLS REVERSE MUCOCUTANEOUS AGING

[75] Inventor: Carl R. Thornfeldt, Nampa, Id.

[73] Assignee: Cellegy Pharmaceuticals, Inc., So. San Francisco, Calif.

[21] Appl. No.: 09/089,302

[22] Filed: Jun. 1, 1998

Related U.S. Application Data

[60] Provisional application No. 60/047,360, Jun. 2, 1997, and provisional application No. 60/056,282, Sep. 3, 1997.

[51] Int. Cl.[7] ........................... A61K 33/32; A61K 33/04; A61K 31/44
[52] U.S. Cl. ........................... 424/642; 424/702; 514/301
[58] Field of Search ..................................... 424/642, 702; 514/301

[56] References Cited

U.S. PATENT DOCUMENTS 5,686,489   11/1997   Yu et al. .................................. 514/557

OTHER PUBLICATIONS

T. Sakamoto et al., "Shampoos Containing Vitamin E Acetate and Dandruff–Controlling Agents," *Chemical Abstracts* (Oct. 24, 1986) 106, Abstract 106:55622.

*Primary Examiner*—Kimberly Jordan
*Attorney, Agent, or Firm*—Townsend and Townsend and Crew LLP

[57] ABSTRACT

This invention provides compositions and methods for preventing and reversing the signs and symptoms of intrinsic and photo aging. The compositions include one or more pyridine-thiols and tautomers with attached metallic moieties. Administration of the compounds to aging skin and mucous membranes in topical formulations, either as the only active ingredient or in combination with other known active ingredients, prevents and reverses aging symptoms. Additional compositions for preventing and reversing aging contain one or more sulfides and oxides of these same metallic ions, either alone or in combination with other molecules known or suspected to exhibit age reversing properties. Topical formulations containing both a pyridine-thiol and tautomers with attached metallic moiety and a metallic sulfide and/or metallic oxide effectively prevent and reverse the signs and symptoms of mucocutaneous aging.

43 Claims, No Drawings

PYRIDINE-THIOLS REVERSE MUCOCUTANEOUS AGING

CROSS-REFERENCE TO RELATED APPLICATIONS

This application claims priority to U.S. Provisional Application Ser. No. 60/047,360, filed Jun. 2, 1997, and also to U.S. Provisional Application Ser. No. 60/056,282, filed Sep. 3, 1997. These applications are incorporated herein by reference for all purposes.

BACKGROUND OF THE INVENTION

1. Field of the Invention

This invention pertains to the field of treating and preventing signs and symptoms of aging.

2. Background

Therapeutic products comprising metallic moieties have been used for many years for a variety of skin diseases. These medications have continued to be used to treat one or several skin diseases. For example, zinc pyrithione (zinc pyridine-2-thiol-1-oxide) is a therapeutic molecule that is used as the active ingredient in the most widely Distributed commercially available medicated shampoos for treatment of dandruff and seborrheic dermatitis. In the past year, this compound has been introduced by two companies in a topical leave-on product to treat scalp psoriasis. Zinc pyrithione has multiple mechanisms of action including antiproliferative, keratolytic, astringent, antibacterial and anti-yeast properties. Zinc undecylenate has also been used as an antifungal agent. Zinc oxide has also had a long history as a sunblock and skin protectant especially for the diaper area. Zinc lactate 0.15% is one component of a prescription product which also comprises erythromicin 2% in a topical therapy for acne vulgaris.

U.S. Pat. No. 4,307,089 discusses a formulation that contains zinc pyrithione and/or its tautomeric form combined with undecylenic acid and the use of the formulation to treat dandruff. U.S. Pat. No. 5,284,649 discusses the use of heavy metal salts of hydroxypyridine thiones and their tautomeric forms, including zinc, zirconium, cadmium, tin, magnesium, sodium, calcium, aluminum and potassium pyrithione, as human deodorants.

Zinc is an essential mineral for animal cell growth and regeneration due to its integral structural role in certain enzymes especially proteases including carboxypeptidase A. Furthermore, the deoxyribonucleic acid (DNA) contains zinc finger binding domains utilized in transcription thus regulating gene activity. This element also functions as an enzyme activator, a coenzyme, and an antioxidant. Zinc and other bivalent ions including cobalt, copper, nickel, and manganese inhibit the binding of triiodothyronine lo its nuclear receptor. Zinc, selenium, vanadium, and chromium all have documented insulin mimetic activity.

Selenium is a known antioxidant utilized as an immune modulator in naturpathic and lay medicine. Its major mechanism of action is via covalent binding to the key detoxification/antioxidant enzyme glutathione peroxidase. Multiple selenium sulfide shampoos have been on the prescription and over-the-counter markets for years to treat dandruff and seborrheic dermatitis. The difference between the two markets is that the prescription product has a much higher concentration of the selenium sulfide. These products are generally considered to be more effective than zinc pyrithione because of documented superior anti-microbial activity.

Multiple enzymes are known to require metallic ions as cofactors or are needed as catalysts. Several other of metals currently are or have been in the past used a human disease medicines. Arsenic was a major topical treatment for psoriasis prior to the advent of corticosteriods. Gallium formulations injected intravenously are used in human medical diagonstic tests. Copper and silver salts are the active ingredients ir topical products for cleansing and deodorizing stomas and burns. Strontium has been reported to treat stinging/burning due to neurogenic inflammation but is associated with bone deposition and marrow suppression.

Use of these metallic compounds as therapeutic compounds would be expected to have serious drawbacks because several, including nickel, chromium, and cobalt, are potent contact sensitizers of the skin and mucous membranes. Iron is a potent oxidant inducing cell damage. Bromine often induces a characteristic dermatosis known as bromoderma. High calcium levels in the stratum corneum inhibit normal barrier formation and desquamation.

Chronologically aged (intrinsic aging) mucocutaneous surfaces show a slight atrophy of the epidermis with straightening of the rete pegs thus weakening the dermal/epidermal junction measured by a decrease in the threshold for suction bullae. There is a moderate decrease in the number of Langerhans cells. Dryness of the skin is a common phenomenon. In the dermis there is lower cellularity and a decrease in elastic fibers and thus in skin elasticity. Capillaries are also fragile as evidenced by bruisability. Collagen metabolism is slower, and there is a progressive lowering in concentration of glycosaminoglycans. Wrinkling occurs, but it tends to be in the form of fine wrinkles that disappear temporarily with stretching. There is a decreased ability to mount inflammatory response and an increase in the time of healing after injury.

Photoaging induces deep wrinkles not erased by stretching, pigmentary alterations with areas of hyper- and hypopigmentation (actinic lentigines and leukodermas), and a variety of benign, premalignant, and malignant neoplasms. The dermis shows evidence of chronic inflammation with increased cellularity and enlarged fibroblasts. Elastotic degeneration occurs in which parts of the upper dermis is occupied by a basophilic fibrous material separating the dermis from the epidermis. This "grenz" zone is interpreted as a repair area. Glycosaminoglycan concentrations is increased, while elastin concentration is increased and arranged in atypical clumps. Collagen fibers are fragmented.

A need exists for methods and compositions that are effective in preventing and/or reversing signs and symptoms of aging. The present invention fulfills these and other needs.

SUMMARY OF THE INVENTION

The invention provides methods of treating or preventing symptoms and signs of aging on a mucocutaneous tissue. In some embodiments, the methods involve topically applying to an affected area of the mucocutaneous tissue a therapeutically effective amount of a topical formulation that contains a metal ion associated with a compound selected from the group consisting of a pyridine-thiol and a tautomer of a pyridine-thiol.

In additional embodiments, the invention provides methods for treating or preventing symptoms of aging on a mucocutaneous tissue by topically applying to an affected area of the mucocutaneous tissue a therapeutically effective amount of a topical formulation comprising at least one of a metal oxide or a metal sulfide.

The invention also provides compositions that can be used to treat or prevent signs and symptoms of aging. In some embodiments, the topical formulations contain (a) a metal ion associated with a compound selected from the group consisting of a pyridine-thiol and a tautomer of a pyridine-thiol; and (b) one or more compounds which are effective in treating symptoms of aging of mucocutaneous tissue.

In other embodiments, the topical formulations contain (a) a metal cation and an anion selected from the group consisting of an oxide and a sulfide; and one or more compounds which are effective in treating symptoms of aging of mucocutaneous tissue.

The invention also provides methods for treating or preventing signs or symptoms of aging by topically applying to an affected area of the mucocutaneous tissue a therapeutically effective amount of a topical formulation containing: (a) a metal ion associated with a compound selected from the group consisting of a pyridine-thiol and a tautomer of a pyridine-thiol; and (b) a metal oxide or a metal sulfide. Topical formulations that contain these ingredients are also provided.

DETAILED DESCRIPTION

Definitions

The term "therapeutically effective amount" or "effective amount" is used herein to denote any amount of a topical formulation which will cause a substantial improvement in a disease condition (such as a subsidence of a lesion, for example) when applied to the affected area. A single application can be sufficient, or the formulation can be applied repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

A "cosmeceutical" is a product, typically non-prescription, that is utilized in the cosmetic industry which produces measurable structural changes in the skin and mucous membranes.

DESCRIPTION OF THE PREFERRED EMBODIMENTS

The present invention provides methods and compositions that are useful for treating or preventing signs and symptoms of aging. The compositions of the invention contain one or more anti-aging compounds that are metal ions complexed with either pyridine thiols or are metal sulfides or metal oxides. The compositions are typically applied to skin or mucous membranes to prevent or treat the aging symptoms, which can be a result of chronologic (intrinsic) aging or photoaging.

A. Anti-Aging Compounds and Formulations

The anti-aging compounds of the invention include pyridine-thiols, as well as tautomers of the pyridine thiols, that are associated with a metal ion. In other embodiments, the anti-aging compounds of the invention are metal ions associated with a sulfide ion or an oxide ion. In other embodiments, the formulations of the invention include combinations of the pyridine-thiol oxides and sulfides and tautomers. The zinc pyrithione and selenium pyrithione combination preferred. Furthermore, this invention includes metallic sulfides and metallic oxides in combination as well as with pyridine-thiol with attached metallic ion or its tautomers. Selenium sulfide with zinc pyrithione is preferred.

The metal ions that can be included in the anti-aging compounds of the invention are, for example, copper, manganese, vanadium, strontium, sodium, silver, cadmium, calcium, titanium, tin, gallium, germanium, scandium, arsenic, aluminum, magnesium, bromine, cobalt, nickel, chromium, potassium, and iron. Zirconium, zinc, strontium, silver, selenium, copper, manganese, gallium, titanium sodium, potassium, vanadium, magnesium, calcium, and arsenic are preferred. Zinc, strontium, silver, selenium and copper are most preferred.

1. Pyridine Thiols

In some embodiments, the formulations of the invention include pyridine-thiols and/or tautomers of the pyridine thiols. Examples of suitable pyridine thiols include, for example, zinc pyrithione, selenium pyrithione, silver pyrithione, and copper pyrithione. Zinc pyridine-2-thiol-1-oxide (pyrithione) is a preferred pyridine thiol.

2. Metal Sulfides and Oxides

The sulfides and oxides of the metallic ions that have activity against symptoms and signs of aging include, for example, any combination of a sulfide or an oxide moiety associated with a metal as set forth above. Particularly preferred compounds include selenium sulfide and zinc oxide.

3. Formulations and Dosages

Typically, the anti-aging compositions described herein will be in the form of a topical formulation for delivering the active ingredient. The formulation will typically contain the anti-aging compound in concentrations that range from about 0.001% to about 60.0% by weight, with about 0.025% to about 20.0% by weight preferred, and about 0.1% to about 5.0% by weight the most preferred. The formulations generally also include a non-toxic, pharmaceutically and/or cosmeceutically acceptable carrier. See, e.g., DRUG FACTS AND COMPARISONS, Published by Facts and Comparisons, A Wolters Kluwer Company (1997) and DERMATOLOGICAL FORMULATIONS: PERCUTANEOUS ABSORPTION, Barry (ed.), Marcel Dekker Inc. (1983).

The local absorption and efficacy of the anti-aging compounds; can be further enhanced by incorporating an appropriate amount of an excipient which can allow increased penetration of, or assist in the delivery of therapeutic molecules across, the stratum corneum permeability barrier of the skin. Many of these penetration enhancing molecules are known to those trained in the art of topical formulation. Examples include humectants such as urea and glycols such as propylene glycol, alcohols including ethanol, fatty acids such as oleic acid, surfactants such as isopropyl myristate and sodium lauryl sulfate, pyrrolidones, glycerol monolaurate, sulfoxides, terpenes including menthol, amines, amides, alkanes, alkanols, Orgelase and water. Vegetable oils or botanical oils containing high unsaturated fatty acids, e.g. safflower oil, olive oil, avocado oil, wheat germ oil, etc. or other chemicals can also facilitate absorption and delivery of compounds.

Pharmaceutically and cosmeceutically acceptable carriers will include water, saline, buffers, and other compounds described, e.g., in the MERCK INDEX, Merck & Co., Rahway, N.J. See, also, BIOREVERSIBLE CARRIERS IN DRUG DESIGN, THEORY AND APPLICATION, Roche (ed.), Pergamon Press, (1987). Various considerations are described, e.g., in Gilman et al. (eds) (1990) GOODMAN AND GILMAN'S: THE PHARMACOLOGICAL BASES OF THERAPEUTICS, 8th Ed., Pergamon Press; NOVEL DRUG DELIVERY SYSTEMS, 2nd Ed., Norris (ed.) Marcel Dekker Inc. (1989), and REMINGTON'S PHARMACEUTICAL SCIENCES, the full disclosures of which are incorporated herein by reference. For standard dosages of conventional pharmacological agents, see, e.g., PHYSICIANS DESK REFERENCE (1997 Edition); and American Medical Association (1997) *Drug Evaluations* (Subscriptions).

The anti-aging compounds of the invention can be administered in a variety of forms. These include, for example, solid, semi-solid and liquid dosage forms, such as tablets, pills, powders, liquid solutions or suspensions, liposomes, nasal/aerosolized dosage forms, implants, injectable and infusible solutions. These agents can also be incorporated into various cosmetic and toiletry formulations (See, e.g., Flick E.W. COSMETIC AND TOILETRY FORMULATIONS, 2nd Ed., Noyes Publications, 1989). The preferred form depends on the intended mode of administration and therapeutic or cosmetic application.

Dosage forms for the topical administration of the compositions of the invention include various mixtures and combinations that can be applied topically and will permit even spreading and absorption into the cutaneous and mucosal surfaces. Examples include sprays, mists, aerosols, lotions, creams, solutions, gels, ointments, pastes, unguents, emulsions and suspensions. The active compound can be mixed under sterile conditions with a cosmeceutically or pharmaceutically acceptable carrier, and with any preservatives, buffers, or propellants which may be required. Topical preparations can be prepared by combining the anti-aging compounds with conventional pharmaceutical and/or cosmeceutical diluents and carriers commonly used in topical dry, liquid, cream and aerosol formulations. Ointment and creams can, for example, be formulated with an aqueous or oily base with the addition of suitable thickening and/or gelling agents. Such bases can include water and/or an oil such as liquid paraffin or a vegetable oil such as peanut oil or castor oil. Thickening agents which can be used according to the nature of the base include soft paraffin, aluminum stearate, cetostearyl alcohol, propylene glycol, polyethylene glycols, woolfat, hydrogenated lanolin, beeswax, and the like. Lotions can be formulated with an aqueous or oily base and will, in general, also include one or more of the following: stabilizing agents, emulsifying agents, dispersing agents, suspending agents, thickening agents, coloring agents, perfumes, and the like. Powders can be formed with the aid of any suitable powder base, e.g., talc, lactose, starch, and the like. Drops can be formulated with an aqueous base or non-aqueous base, and can also include one or more dispersing agents, suspending agents, solubilizing agents, and the like.

The ointments, pastes, creams and gels also can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Solutions of anti-aging compound can be converted into aerosols or sprays by any of the known means routinely used for making aerosol inhalant pharmaceuticals. In general, such methods comprise pressurizing or providing a means of pressurizing a container of the solution, usually with an inert carrier gas, and passing the pressurized gas through a small orifice. Sprays can additionally contain customary propellants, such as chlorofluorohydrocarbons and volatile unsubstituted hydrocarbons, such as butane and propane.

Multiple inactive ingredients are generally incorporated in topical formulations to improve cosmetic acceptability, and are optional ingredients in the formulations of this invention. Examples of ingredients are emulsifiers, humectants, surfactants, preservatives, fragrances, coloring agents, emollients, and fillers.

The topical pharmaceutical compositions can also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

One example of a topical formulation contains, in addition to the anti-aging agent, light mineral oil, sorbitol solution, hydroxyoctacosanyl hydroxystearate, methoxy PEG-22/dodecyl glycol copolymer, stearoxytrimethylsilane and stearic alcohol, dimethicone 50 cs, fragrance, methylparaben, edetate disodium, quarterium-15, butylates hydroxytoluene, citric acid (monohydrate) and purified water.

The dosage of a specific anti-aging compound depends upon many factors that are well known to those skilled in the art, for example, the particular compound; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

Because the anti-aging compounds of the invention are each effective alone, the compositions can be essentially free of other agents that are effective against aging symptoms on mucocutaneous membranes. In some embodiments, however, the compositions include additional agents that are known, reported, or suspected to display anti-aging activity. Such molecules include, for example, keratolytics such as hydroxy acids and their lactones, ketoacids, phenolics, amino acids, carboxylic acids, antioxidants, vitamins A, C, E, certain nutrients, metallic elements, anti-inflammatory agents, and the esters, amides, aldehydes, salts, analogs, isomers and derivatives thereof. Examples of specific anti-aging active ingredients that can be additionally incorporated into formulations of this invention include, for example, alpha, beta, gamma and poly-hydroxy and keto acids as well as tretinoin, retinol, retinoldehyde, ascorbic acid, tocopherol, dicarboxylic acids, lactones of hydroxy acids, kojic acids, other carboxylic acids, including linoleic, compounds with a phenol ring as the primary active structure, derivatives of phenol, chloroacetic acids, corticosteroids, nonsteroidal anti-inflammatory agents, sulfones, catechins and other antioxidants, amino acids and other minerals, and the esters, amides, salts, analogs, aldehydes, isomers, and derivatives thereof.

In preferred embodiments, the additional anti-aging agents included in combination formulations of this invention include esters, ethers and amides of salicylic, benzilic, malic, citric, tartaric, pyruvic, glycolic, lactic, glucuronic, tropic, linoleic, linolenic, azelaic, kojic, ascorbic, mandelic, benzoic, acetic, formic, fumaric, oxalic, propanoic, succinic, galatonic, galacturonic, glucuronic, glyceric, mucic, succharic, tartaronic, allolactic, phenyllactic, tetrahydroxypentanoic and hexahydroxyheptanoic acids, gluconolactone, tocopherol, retinol, tretinoin, retinaldehyde, vitamin D analogs, glucocorticosteroids, colchicine, trichlorocetic and dichloracetic acids, ibuprofen, ketoprofen, ketorolac, piroxicam, indomethacin, serine, alanine, glycine, arginine, phenol, thymol, menthol, eucalyptol, methylresorcinol, hexylresorcinol, resorcinol, 3-hydroxy butyric acid, 4-hydroxyvaleric acid, dapsone and epigallocatechingallate. The additional items in the preceding list are examples only; the list is not intended to be inclusive of all compounds that are known, reported, or suspected to display activity in reversing the signs of aging of the skin and mucous membranes.

B. Methods for Treating or Preventing Signs and Symptoms of Aging

The invention also provides methods for treating signs and symptoms of aging of the skin and mucosal membranes. The treatments involve administering an effective amount of an anti-aging compound of the invention as described herein, typically as a topical formulation. The formulations of this invention are generally applied to the locally affected diseased or abnormal skin or mucous membranes.

The methods described herein find use in the treatment and/or prevention of a variety of signs and symptoms of aging. Such signs and symptoms against which the methods are effective include, but are not limited to, wrinkling, irregular pigmentation, laxity, inelasticity, fragility, roughness, poor wound healing, and neoplasia.

To treat or prevent an aging-related condition of the skin or mucosal membrane, a composition that contains one or more concentrated inflammation modifiers is administered to the skin or mucosal membrane in an amount effective to modulate the inflammatory condition. An effective amount can be determined by applying the compositions containing the anti-inflammatory agent to test animal models a, described herein. Typically, the compositions that are useful in the claimed methods include one or more concentrated inflammation modifiers at a concentration of between 0.001% and 100%. Preferably the concentrated inflammation modifier concentration will be between about 0.15% and about 15%. The compositions can also include additional ingredients, as described below, but an additional anti-inflammatory agent is not generally required. For example, for acute diseases such as allergic and irritant contact dermatitis, the inflammatory reaction can be prevented by prophylactic application of the described concentrated inflammation modifiers, either alone or in combination with a penetration blocking agent.

EXAMPLES

The following examples are offered to illustrate, but not to limit the present invention.

Example 1

Formulation A

A 0.25% zinc pyrithione lotion was produced by dissolving 2.5 mg of zinc-1-hydroxypyridine-2-thione (Sigma: St. Louis, Mo.) in 100 milliliters of 60% (ethanol, 25% propylene glycol and 15% water. This emulsion was designed to be thoroughly shaken prior to topical application to affected mucocutaneous surface. Once applied, Formulation A was allowed to dry for 3 to 5 minutes; glycerin was then applied sparingly to cover the whole surface.

Example 2

Application

Three middle aged patients afflicted with mild acne vulgaris with about 10 inflammatory lesions on each side of the face and moderate fine wrinkling, irregular pigmentation, and loss of elasticity were treated with Formulation A twice daily for 12 weeks. All patients experienced complete clearing of the acne lesions and noticeable decrease in the degree and number of wrinkles and pigmentation with improvement in elasticity.

Example 3

Formulation B

Formulation A was adjusted to Formulation B by adding 5 ml of salicylic acid (Sigma: St. Louis, Mo.) by weight to make a 0.5% solution. Each application was performed as in Example 1 above.

Example 4

Application

Two middle aged patients were treated with Formulation B twice daily for 16 weeks. Both experienced a moderate diminution of fine wrinkling, irregular pigmentation, and improved skin texture.

Example 5

Formulation C

Formulation C was prepared by dissolving 25 milligrams of selenium sulfide (Sigma: St. Louis, Mo.) in 100 milliliters of 60% ethanol, 25% propylene glycol, and 15% water to make a 2.5% by weight selenium sulfide solution. Each application was performed as in Example 1 above.

Example 6

Application

Two middle aged males suffered from skin aging experienced moderate improvement in all signs with twice daily application of Formulation C for 16 weeks.

Example 7

Application

Three patients suffering from frequently recurrent facial seborrheic dermatitis and moderate signs of aging applied Formulation C twice daily for 16 weeks. There was complete clearing of the dermatitis with no recurrences during this period. All patients experienced moderately improved texture and diminished fine wrinkles.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for treating a symptom of aging on a mucocutaneous tissue, the method comprising topically applying to an affected area of the mucocutaneous tissue a therapeutically effective amount of a topical formulation comprising a metal ion associated with a compound selected from the group consisting of a pyridine-thiol and a tautomer of a pyridine-thiol.

2. The method of claim 1, wherein the aging is selected from the group consisting of chronologic aging and photoaging.

3. The method of claim 1, wherein the metal ion is selected from the group consisting of zirconium, zinc, vanadium, titanium, tin, strontium, silver, sodium, selenium, scandium, potassium, magnesium, manganese, nickel, germanium, gallium, copper, calcium, cadmium, cobalt, chromium, iron, bromine, aluminum and arsenic.

4. The method of claim 1, wherein the topical formulation comprises about 0.001% to about 60% by weight pyridine-thiol and pyridine-thiol tautomer.

5. The method of claim 1, wherein the symptom of aging is selected from the group consisting of wrinkling, irregular pigmentation, laxity, inelasticity, fragility, roughness, poor wound healing, and neoplasia.

6. The method of claim 1, wherein the topical formulation comprises about 0.1% to about 5% by weight of a compound selected from the group consisting of zinc pyrithione, silver pyrithione, selenium pyrithione, and copper pyrithione.

7. The method of claim 6, wherein the topical formulation comprises about 2.5% by weight of zinc pyrithione.

8. The method of claim 1, wherein the topical formulation is applied in a form selected from the group consisting of a spray, a mist, an aerosol, a solution, a lotion, a gel, a cream, an ointment, a paste, an unguent, an emulsion, and a suspension.

9. The method of claim 1, wherein the topical formulation further comprises one or more additional compounds which are effective in treating symptoms of aging.

10. The method of claim 9, wherein the additional compound is selected from the group consisting of alpha-, beta-, gamma-, and polyhydroxy and keto acids, retinol, retinaldehyde, tretinoin, ascorbic acid, tocopherol, dicarboxylic acids, kojic acids, other carboxylic acids, chloroacetic acids, compounds having a phenol ring as an primary active structure, derivatives of phenol, corticosteroids, non-steroidal anti-inflammatory agents, sulfones, catechins and other antioxidants, amino acids, other minerals and nutrients, lactones, and esters, amides, salts, analogs, aldehydes, isomers and derivatives thereof.

11. The method of claim 10, wherein the additional compound is present in the topical formulation at a concentration of 0.01% to 99.9% by weight.

12. The method of claim 9, wherein the additional compound is selected from the group consisting of salicylic, benzilic, malic, citric, tartaric, tropic, glucuronic, mandelic, benzoic, acetic, formic, fumaric, oxalic, propanoic, succinic, galactonic, galacturonic, glucoronic, glyceric, mucic, succharic, tartaronic, allolactic, phenyllactic, pyruvic, glycolic, lactic, linoleic, linolenic, azelaic, kojic, ascorbic, trichloroacetic, and dichloracetic, tetrahydroxypentanoic and hexahydroxyheptanoic acids, glucoconolactone, tocopherol, retinol, retinaldehyde, tretinoin, vitamin D analogs, trichlorocetic acid, glucocorticosteroids, colchicine, ibuprofen, ketoprofen, ketorolac, piroxicam, indomethacin, serine, alanine, glycine, phenol, arginine, thymol, dapsone, menthol, eucalyptol, resorcinol, methyl resorcinol, hexyl resorcinol, 3-hydroxy butyric acid, 4-hydroxyvaleric acid, epigallocatechingallate, and esters, ethers, amides, analogs, derivatives, aldehydes, isomers and salts thereof.

13. The method of claim 12, wherein the additional compound is present in the topical formulation at a concentration of 0.5% to 30.0% by weight.

14. The method of claim 1, wherein the metal ion is selected from the group consisting of zirconium, vanadium, titanium, tin, strontium, silver, sodium, selenium, scandium, potassium, magnesium, manganese, nickel, germanium, gallium, copper, calcium, cadmium, cobalt, chromium, iron, bromine, aluminum and arsenic.

15. The method of claim 1, wherein the topical formulation comprises about 0.1% to about 5% by weight of a compound selected from the group consisting of silver pyrithione, selenium pyrithione, and copper pyrithione.

16. A topical formulation for treating a symptom of aging on a mucocutaneous tissue, the formulation comprising:
(a) a metal ion associated with a compound selected from the group consisting of a pyridine-thiol and a tautomer of a pyridine-thiol; and
(b) one or more compounds which are effective in treating symptoms of aging of mucocutaneous tissue.

17. The topical formulation of claim 16, wherein the metal ion is selected from the group consisting of zirconium, zinc, vanadium, titanium, tin, strontium, silver, sodium, selenium, scandium, potassium, magnesium, manganese, nickel, germanium, gallium, copper, calcium, cadmium, cobalt, chromium, iron, bromine, aluminum and arsenic.

18. The topical formulation of claim 16, wherein the topical formulation comprises about 0.1% to about 5% by weight of a compound selected from the group consisting of zinc pyrithione, silver pyrithione, selenium pyrithione, and copper pyrithione.

19. The topical formulation of claim 16, wherein the additional compound is selected from the group consisting of salicylic, benzilic, malic, citric, tartaric, tropic, glucuronic, mandelic, benzoic, acetic, formic, fumaric, oxalic, propanoic, succinic, galactonic, galacturonic, glucoronic, glyceric, mucic, succharic, tartaronic, allolactic, phenyllactic, pyruvic, glycolic, lactic, linoleic, linolenic, azelaic, kojic, ascorbic, trichloroacetic, and dichloracetic, tetrahydroxypentanoic and hexahydroxyheptanoic acids, glucoconolactone, tocopherol, retinol, retinaldehyde, tretinoin, vitamin D analogs, trichlorocetic acid, glucocorticosteroids, colchicine, ibuprofen, ketoprofen, ketorolac, piroxicam, indomethacin, serine, alanine, glycine, phenol, arginine, thymol, dapsone, menthol, eucalyptol, resorcinol, methyl resorcinol, hexyl resorcinol, 3-hydroxy butyric acid, 4-hydroxyvaleric acid, epigallocatechingallate, and esters, ethers, amides, analogs, derivatives, aldehydes, isomers and salts thereof.

20. The topical formulation of claim 16, wherein the metal ion is selected from the group consisting of zirconium, vanadium, titanium, tin, strontium, silver, sodium, selenium, scandium, potassium, magnesium, manganese, nickel, germanium, gallium, copper, calcium, cadmium, cobalt, chromium, iron, bromine, aluminum and arsenic.

21. The topical formulation of claim 16, wherein the topical formulation comprises about 0.1% to about 5% by weight of a compound selected from the group consisting of silver pyrithione, selenium pyrithione, and copper pyrithione.

22. A method for treating a symptom of aging on a mucocutaneous tissue, the method comprising topically applying to an affected area of the mucocutaneous tissue a therapeutically effective amount of a topical formulation comprising at least one of a metal oxide or a metal sulfide.

23. The method of claim 22, wherein the aging is selected from the group consisting of chronologic aging and photoaging.

24. The method of claim 22, wherein the metal ion is selected from the group consisting of zirconium, zinc, vanadium, titanium, tin, strontium, silver, sodium, selenium, scandium, potassium, magnesium, manganese, nickel, germanium, gallium, copper, calcium, cadmium, cobalt, chromium, iron, bromine, aluminum and arsenic.

25. The method of claim 22, wherein the topical formulation comprises between about 0.001% and about 60% by weight of the metal oxide or metal sulfide.

26. The method of claim 25, wherein the topical formulation comprises from about 0.025% to about 20% by weight of the metal oxide or metal sulfide.

27. The method of claim 26, wherein the topical formulation comprises from about 0.1% to about 5% by weight of zinc oxide or selenium sulfide.

28. The method of claim 27, wherein the topical formulation comprises about 0.2% by weight of selenium sulfide.

29. The method of claim 26, wherein the topical formulation comprises from about 0.1% to about 5% by weight of zinc oxide.

30. The method of claim 22, wherein the symptom of aging is selected from the group consisting of wrinkling, irregular pigmentation, laxity, inelasticity, fragility, roughness, poor wound healing, and neoplasia.

31. The method of claim 22, wherein the topical formulation is applied in a form selected from the group consisting of a spray, a mist, an aerosol, a solution, a lotion, a gel, a cream, an ointment, a paste, an unguent, an emulsion, and a suspension.

32. The method of claim 22, wherein the topical formulation further comprises one or more additional compounds which are effective in treating symptoms of aging.

33. The method of claim 32, wherein the additional compound is selected from the group consisting of alpha-, beta-, gamma-, and polyhydroxy and keto acids, retinol, retinaldehyde, tretinoin, ascorbic acid, tocopherol, dicarboxylic acids, kojic acids, other carboxylic acids, chloroacetic acids, compounds having a phenol ring as an primary active structure, derivatives of phenol, corticosteroids, nonsteroidal anti-inflammatory agents, sulfones, catechins and other antioxidants, amino acids, other minerals and nutrients, lactones, and esters, amides, salts, analogs, aldehydes, isomers and derivatives thereof.

34. The method of claim 32, wherein the additional compound is selected from the group consisting of salicylic, benzilic, malic, citric, tartaric, tropic, glucuronic, mandelic, benzoic, acetic, formic, fumaric, oxalic, propanoic, succinic, galactonic, galacturonic, glucoronic, glyceric, mucic, succharic, tartaronic, allolactic, phenyllactic, pyruvic, glycolic, lactic, linoleic, linolenic, azelaic, kojic, ascorbic, trichloroacetic, and dichloracetic, tetrahydroxypentanoic and hexahydroxyheptanoic acids, glucoconolactone, tocopherol, retinol, retinaldehyde, tretinoin, vitamin D analogs, trichlorocetic acid, glucocorticosteroids, colchicine, ibuprofen, ketoprofen, ketorolac, piroxicam, indomethacin, serine, alanine, glycine, phenol, arginine, thymol, dapsone, menthol, eucalyptol, resorcinol, methyl resorcinol, hexyl resorcinol, 3-hydroxy butyric acid, 4-hydroxyvaleric acid, epigallocatechingallate, and esters, ethers, amides, analogs, derivatives, aldehydes, isomers and salts thereof.

35. The method of claim 22, wherein the metal ion is selected from the group consisting of zirconium, zinc, vanadium, titanium, tin, strontium, silver, sodium, scandium, potassium, magnesium, manganese, nickel, germanium, gallium, copper, calcium, cadmium, cobalt, chromium, iron, bromine, aluminum and arsenic.

36. A topical formulation comprising:
(a) a metal cation and an anion selected from the group consisting of an oxide and a sulfide; and
(b) one or more compounds which are effective in treating symptoms of aging of mucocutaneous tissue.

37. The topical formulation of claim 36, wherein the metal cation is selected from the group consisting of zirconium, zinc, vanadium, titanium, tin, strontium, silver, sodium, selenium, scandium, potassium, magnesium, manganese, nickel, germanium, gallium, copper, calcium, cadmium, cobalt, chromium, iron, bromine, aluminum and arsenic.

38. The topical formulation of claim 37, wherein the topical formulation comprises one or more compounds selected from the group consisting of zinc oxide and selenium sulfide.

39. The topical formulation of claim 37, wherein the topical formulation comprises zinc oxide.

40. The topical formulation of claim 36, wherein the additional compound is selected from the group consisting of alpha-, beta-, gamma-, and polyhydroxy and keto acids, retinol, retinaldehyde, tretinoin, ascorbic acid, tocopherol, dicarboxylic acids, kojic acids, other carboxylic acids, chloroacetic acids, compounds having a phenol ring as an primary active structure, derivatives of phenol, corticosteroids, nonsteroidal anti-inflammatory agents, sulfones, catechins and other antioxidants, amino acids, other minerals and nutrients, lactones, and esters, amides, salts, analogs, aldehydes, isomers and derivatives thereof.

41. The topical formulation of claim 36, wherein the metal cation is selected from the group consisting of zirconium, zinc, vanadium, titanium, tin, strontium, silver, sodium, scandium, potassium, magnesium, manganese, nickel, germanium, gallium, copper, calcium, cadmium, cobalt, chromium, iron, bromine, aluminum arid arsenic.

42. A method for treating a symptom of aging on a mucocutaneous tissue, the method comprising topically applying to an affected area of the mucocutaneous tissue a therapeutically effective amount of a topical formulation comprising:
(a) a metal ion associated with a compound selected from the group consisting of a pyridine-thiol and a tautomer of a pyridine-thiol; and
(b) a metal oxide or a metal sulfide.

43. A topical formulation for treating a symptom of aging on a mucocutaneous tissue, the topical formulation comprising:
(a) a metal ion associated with a compound selected from the group consisting of a pyridine-thiol and a tautomer of a pyridine-thiol; and
(b) a metal oxide or a metal sulfide.

* * * * *